(12) United States Patent
Petiard et al.

(10) Patent No.: US 8,378,090 B2
(45) Date of Patent: *Feb. 19, 2013

(54) PRODUCTION OF GLUCOSAMINE FROM PLANT SPECIES

(75) Inventors: Vincent Petiard, Tours (FR); Stephane Michaux, Monnaie (FR); Didier Courtois, St-Avertin (FR)

(73) Assignee: Nestec S.A., Vevey (CH)

( * ) Notice: Subject to any disclaimer, the term of this patent is extended or adjusted under 35 U.S.C. 154(b) by 803 days.

This patent is subject to a terminal disclaimer.

(21) Appl. No.: 11/913,153

(22) PCT Filed: May 12, 2006

(86) PCT No.: PCT/EP2006/004467
§ 371 (c)(1),
(2), (4) Date: Dec. 19, 2007

(87) PCT Pub. No.: WO2006/120007
PCT Pub. Date: Nov. 16, 2006

(65) Prior Publication Data
US 2008/0214803 A1 Sep. 4, 2008

(51) Int. Cl.
*C07H 5/04* (2006.01)
*C07H 5/06* (2006.01)

(52) U.S. Cl. ............................................. 536/55.2

(58) Field of Classification Search ............ 536/55.2
See application file for complete search history.

(56) References Cited

U.S. PATENT DOCUMENTS

| | | | |
|---|---|---|---|
| 5,866,142 A | 2/1999 | Riordan | |
| 5,916,622 A * | 6/1999 | Ecochard | 426/596 |
| 5,998,173 A | 12/1999 | Haynes et al. | |
| 6,372,457 B1 | 4/2002 | Berry et al. | |
| 6,413,525 B1 | 7/2002 | Mammone et al. | |
| 6,486,307 B1 | 11/2002 | Gandhi et al. | |
| 2002/0119107 A1 | 8/2002 | Varani et al. | |
| 2004/0037901 A1 | 2/2004 | Breton et al. | |
| 2005/0119107 A1 | 6/2005 | Shikata et al. | |

FOREIGN PATENT DOCUMENTS

| | | |
|---|---|---|
| CA | 2607496 | 11/2006 |
| EP | 0923382 | 6/1999 |
| EP | 1 172 041 | 1/2002 |
| GB | 649 791 | 1/1951 |
| JP | 59-013708 | 1/1984 |
| JP | 01102092 | 4/1989 |
| JP | 02174790 | 7/1990 |
| WO | WO 98/06418 | 2/1998 |
| WO | WO 00/74696 | 12/2000 |
| WO | WO 2005/053710 | 6/2005 |

OTHER PUBLICATIONS

Patel, J.R. et al., Journal of Agricultural Science "The effect of various agronomic practices on the yield of chicory (*Cichorium intybus*)", vol. 135, pp. 271-278 (2000).*

Rijck, G. De and Schrevens, E., Scientia Horticulturae "Multifactorial optiimsation of the nutrient solution for hydroponically grown chicory plants", vol. 76, pp. 149-159 (1998).*

Machado et al., "Inulin Production by *Vernonia herbacea* as Influenced by Mineral Fertilization and Time of Harvest," Revista Brasileira de Botanica, vol. 21, No. 3, pp. 275-280 (1998).

Jianhong et al., "Volatile Compounds Formed from Thermal Degradation of Glucosamine in a Dry System," Journal of Agricultural and Food Chemistry, vol. 46, No. 5, pp. 1971-1974 (1998).

* cited by examiner

*Primary Examiner* — Wendy C Haas
(74) *Attorney, Agent, or Firm* — K&L Gates LLP

(57) ABSTRACT

The present invention relates to a process for generating glucosamine from plants wherein fresh plant materials, or rehydrated dried plant materials or plant extracts, are heated at a temperature comprised between 70 and 110° C. for more than 10 hours, characterized in that a fertilizer acting as glucosamine precursor is added during the cultivation of the plants, before the harvest.

10 Claims, No Drawings

PRODUCTION OF GLUCOSAMINE FROM PLANT SPECIES

The present invention relates to a process leading to raw plant materials containing levels of glucosamine equal or higher than 0.5% (wt) of the dry matter.

BACKGROUND OF THE INVENTION

Use of Glucosamine

The use of pure glucosamine in the treatment of joint diseases is widely described in the patent as well as in the scientific literature, usually in combination with other compounds or extracts from various natural sources. Pure glucosamine is added as glucosamine hydrochloride or glucosamine sulphate, and comes from shellfish hydrolysis. For example, WO2000/0074696 describes "herbal compositions comprising glucosamine and *Trypterygium wilfordii, Ligustrum lucidum* and/or *Erycibe schmidtii*, for treating inflammation or degeneration of joint tissues, e.g. arthritis" where pure glucosamine is mixed with plant preparation. Other patents relate to compositions of plant carbohydrates as dietary supplements (EP 1 172 041 or EP 923 382) where glucosamine is originated from chitin, i.e. once again from shellfish hydrolysis.

The use of glucosamine as an anti-osteoarthritis agent has been intensively developed during the last decade. Glucosamine is suspected to be the sole active compound on joint disease such as osteoarthritis (up to recently only symptomatic treatment such as non-steroidal anti-inflammatory drugs have been sought to be efficient).

Glucosamine has also been shown preventing the cartilage degradation by inhibiting the production of MMPs (Matrix metalloproteases) such as MMP1, MMP3 and MMP13. Interestingly glucosamine is also related to the aging process of skin, which has been characterized mainly by the continuous loss of elasticity and the loss of moisture. Skin aging is reflected by major structural changes and variations in composition. Most notably aged skins have less collagen and glycosaminoglycans compared with young skins. Glycosaminoglycan molecules produced by the skin include hyaluronic acid (poly d-glucuronic acid-n-acetyl-d-glucosamine), chondroitin sulfate, and dermatan sulfate. Hyaluronic acid is produced in higher quantities by the skin cells in response to exfoliation. Hyaluronic acid has a large capacity for hydration.

Inhibiting MMP-1 is related to the inhibition of the polyglycan/collagen degradation, and therefore also related to skin ageing: MMP-1 can be induced by UV and is recognized as a marker of the skin ageing. In US 2002/119107, the invention is based on the selective inhibition of MMP-1 claiming topical compositions for protecting human skin from collagen degradation. US 2004/037901 claims a regime for inhibiting the adverse signs of effects of cutaneous aging comprising an extract from rosemary plant inhibiting the expression of metalloproteases.

Glucosamine has been shown to significantly improve dryness of the skin and exfoliation. Glucosamine increases the moisture content and improves the smoothness of the skin. These findings suggest that long-term intake of glucosamine is effective in improving moisture content and smoothness of the skin.

It has been shown that oral supplement containing glucosamine lead to a reduction (34%) in the number of visible wrinkles and (34%) in the number of fine lines in a group of women who took the supplement. The use of an oral supplement containing glucosamine, minerals, and various antioxidant compounds can potentially improve the appearance of visible wrinkles and fine lines.

U.S. Pat. No. 6,413,525 describes methods of substantially exfoliating the skin. In particular, the invention relates to topically applied compositions containing an amino sugar in the form of N-acetyl glucosamine: when young skin cells are exposed after exfoliation, they produce larger quantities of hyaluronic acid which is a glycosaminoglycan composed of a chain of alternating, repeating, D-glucuronic acid and N-acetyl-D-glucosamine molecules. N-acetyl-D-glucosamine is known to be a rate-limiting factor in the hyaluronic acid production by living cells. The topical application of glucosamine assists in the continued production of hyaluronic acid.

Other Compositions for topical application containing N-acetyl-D-glucosamine have also been disclosed for example, in JP 59 013 708 (soften and moisturize the skin) or U.S. Pat. No. 5,866,142 (a composition for exfoliating the skin).

Origin of Glucosamine

Glucosamine, 2-amino-2-deoxy-D-glucose, is a naturally occurring derivative of fructose and is an essential component of glycoproteins and proteoglycans, important constituents of many eukaryotic proteins. This is an essential component of mucopolysaccharides and chitin. Glycosaminoglycans (mucopolysaccharides) are large complexes incorporated into connective tissue, skin, tendons, ligaments and cartilage.

Industrial Sources of Glucosamine

Industrial glucosamine is a pure compound obtained from the acidic hydrolysis of chitin from shellfish, a complex carbohydrate derived from N-acetyl-D-glucosamine. As an example, U.S. Pat. No. 6,486,307 describes an improved method for chitin acidic hydrolysis: a method of producing glucosamine hydrochloride from chitin by grinding the chitin to a very fine size and digesting it with concentrated hydrochloric acid.

Glucosamine can also be produced from enzymatic hydrolysis of shellfish. As an example, U.S. Pat. No. 5,998,173 describes a novel process for directly producing N-acetyl-D-glucosamine from chitin utilizing an ensemble of the chitinase family of enzymes to hydrolyze chitin of crustacean shells.

Patents have also been filed protecting microbial fermentation processes where cultivated microorganisms biosynthesize glucosamine. As an example, U.S. Pat. No. 6,372,457 describes a method and material for producing glucosamine by fermentation using a genetically modified microorganism.

All these processes concern the production of pure, extracted glucosamine, in competition with shellfish extracts.

GB 649 791 relates to improvements in drying chicory. The process according to this patent comprises the steps of:
  cutting chicory roots,
  fermenting the chicory roots under aeraobic conditions at
    temperatures not substantially exceeding 70° C. (best
    temperatures between 50 and 55° C.) for 7 to 8 hours,
    and
  quick drying chicory at 150° C. for about 30 minutes.
  These conditions do not allow to generate glucosamine.

Carvalho et al, in a publication entitled "inulin production by *Vernonia herbacea* as influenced by mineral fertilization and time of harvest" (Revista brasileira de botanica, 1998), showed that the addition of a fertilizer during cultivation of an inulin-containing plant does not enhance the inulin content.

In WO2005/053710, it has been found that glucosamine can be formed from several raw plant materials by following a special drying process, therefore obtaining glucosamine contents of between 150 and 1000 mg per kg dry weight.

SUMMARY OF THE INVENTION

In a first aspect, the present invention describes new processes to obtain glucosamine from plants by using a nitrogen-based fertilizer before harvesting the plant material and submitting it to a heating process. The nitrogen-based fertilizer acts as a precursor of glucosamine, in order to obtain plant raw materials containing level of glucosamine higher than 0.5% (5 g per kg dry weight) of the dry matter. The present invention therefore allows reaching glucosamine content in plant material much higher than previously described in the prior art, for example reflected by WO2005/053710. The consequence is that a less raw plant material or plant extract is required to reach the active dose of glucosamine described in the literature. Therefore, the process is more usable at an industrial scale.

The above-mentioned fertilizers can be added in field or in hydroponic culture systems between few hours up to few weeks before the harvest of the plant material.

DETAILED DESCRIPTION OF THE INVENTION

In the present specification, the word "heating" (and derived "heated") has to be understood as a heating process in the range of temperature of 70-110° C., for more than 10 hours and preferably for less than one week. This heating process can be described as a drying process. The heating process can also consist in a liquid maceration, taking place at the same temperature and time conditions, replacing the drying process.

In the present specification, by "free glucosamine", it has to be understood non-polymerized glucosamine.

In the present specification, by "high amount of glucosamine" it has to be understood that the amount of glucosamine is higher than traces of glucosamine, higher than the amounts in the corresponding fresh (non-dried) material and higher than any content cited in literature or patents. It should be understood as glucosamine present in amounts higher than 0.5% per kg dry matter of raw material.

In the present specification, "plant" and "plant material" are considered as synonyms. By "plant", "plant material" or "plant extract" it has to be understood any plant material capable of generating glucosamine according to the heating process of the invention, and any type of plant extract obtained by any extraction procedure known to the skilled person from said plant material capable of generating glucosamine according to the heating process of the invention. For example, a plant comprising a certain amount of glucosamine can be a dried or rehydrated plant material having undergone the process of the invention. A plant extract comprising a certain amount of glucosamine can be an aqueous solution extracted from said plant having undergone the process of the invention.

Accordingly, in an aspect, the present invention describes new process to obtain glucosamine from plants.

With respect to the first object of the present invention, the plant or plant extract are processed according to the invention in order to contain natural free glucosamine in high amounts.

In a preferred embodiment, the plant or plant extract is from any part of the plant, e.g. leaves, tubers, fruits, seeds, roots, grains or cell cultures. After controlled heating process of the plant raw material, the plant or plant extract may be in the form of a dried, lyophilized extract of leaves, roots and/or fruits depending on the source of plant, or fresh plant, or glucosamine-enriched fraction.

In one embodiment, the cultivation of the plant species is done in fields or in hydroponic culture systems.

In a preferred embodiment, the cultivation of the plant species is done in hydroponic culture systems.

The plant or plant extract is selected for its ability to generate free glucosamine through the process of the present invention; in particular it may be selected from the group consisting of plant species containing sucrose, fructose or inulin such as *Cichorium, Daucus, Helianthus, Beta.*

In one embodiment the plant material or plant extract may be for example from root of Chicory (*Cichorium intybus*), carrot (*Daucus carota*), tuber of Jerusalem artichoke (*Helianthus tuberosum*), root of beet (*Beta vulgaris*).

In a preferred embodiment, the plant species is *Cichorium intybus* used for the production of Belgian endive in fields or in hydroponic culture systems: i.e. chicon, witloof chicory, witloof, French endive, white endive, Dutch chicory, succory, common chicory, or Italian dandelion is *Cichorium intybus*. Witloof chicory is the common name used by most horticulturists for the cultivated plant, while Belgian endive is more used for the product ultimately sold in grocery stores to consumers. Endive is the second growth of the bud from the top of a chicory root. The first growth takes place in the field on a plant grown from seed. The second growth takes place out of the field, usually in a building, in the dark. Each root has one main bud leading to the development of the chicon (endive).

In a most preferred embodiment, the cultivation of chicory is done in hydroponic culture systems. The chicory roots are placed in a recirculating hydroponic solution and the nutrients in this nutritive solution, including the fertilizers responsible for the further glucosamine formation, promote the growth of the feeder roots that sprout from the bottom of the chicory root. These feeder roots act as a pump through the chicory root's vascular system. That is, the skilled person will recognize many variations in this example to cover a wide range of processing, and mixtures to rationally adjust the naturally occurring levels of the compounds of the invention for a variety of applications.

In one embodiment, a current production system of endives is used in the presence of a fertilizer acting as precursor of glucosamine, wherein the roots of chicory are harvested at the same time as the aerial parts (endives).

In another embodiment, after the current commercial production of the endives, the root of chicory are placed again in hydroponic conditions in the presence of a fertilizer acting as precursor of glucosamine.

In one embodiment, fresh plant material treated according to the invention or plant material treated according to the invention, being then dried and subsequently re-hydrated can be used as starting material, and processed to obtain plant material with high glucosamine content according to the present invention.

In a preferred embodiment, fresh plant material is used.

According to the present invention, using with various means a nitrogen-based fertilizer for the growth of the plants acting as precursor of glucosamine, the obtained quantities of glucosamine are much more higher than in WO 2005/053710, (higher than 5 g per kg dry matter of chicory root).

As disclosed in WO2005/053710, the drying process described is one way to obtain glucosamine in plants in large amounts: levels around 500 mg per kg dry matter of chicory root, 100 mg per kg dry matter of carrot root, or 50 mg per kg dry matter of Jerusalem artichoke tubers or beet root can be obtained using the drying process described in WO2005/053710.

Fresh, dried or re-hydrated raw plant materials that have previously been in contact with a nitrogen-based fertilizer during their growth are heated using liquid maceration or drying process at a temperature below 110° C., preferably at temperatures comprised between 70 and 110° C., most preferably between 70 and 91° C. or below for more than 10 hours and preferably less than one week, preferably between 10 and 120 hours, for example between 12 and 50 h, depending on the plant species and plant organ. If the temperatures and/or heating times are too low and/or too short, the generation of glucosamine won't be efficient or will be very slow, leading to a process that will not be economically viable. On the contrary, if the temperatures and/or heating time are too high and/or too long, the glucosamine will be generated but subsequently progressively degraded.

Therefore, the temperatures and times are chosen in order to obtain glucosamine contents of at least 5 g glucosamine/kg of dry matter of the corresponding plant material having undergone the heating process.

A most preferred example comprises a drying in an oven at a temperature of 85° C. between 48 and 72 hours.

The fertilizers used according to the present invention are compounds allowing the formation of the sugar-nitrogen compound condensation required to form glucosamine. Preferably, they consist in ammonium salts. Examples of such ammonium salts are ammonium nitrate or ammonium sulfate, among others. The preferred precursor of glucosamine is ammonium sulfate that has shown surprisingly good results in the process according to the invention.

The fertilizers are used between few hours up to few weeks before the harvest of the plant material. That is, the skilled person will recognize many variations in this example to cover a wide range of application of fertilizer, rationally adjusting the naturally occurring levels of the compounds of the invention for a variety of applications.

For the final process leading to glucosamine formation, a suitable process is described in WO2005/053710 for the preparation of the plant material: the plant material is harvested, cut and dried in an oven or in an industrial dryer at a temperature below 110° C., preferably between 80 and 105° C., most preferably 91° C. or below for more than 10 hours and preferably less than one week, preferably between 10 and 120 hours, for example between 12 and 50 h, depending on the plant species and plant organ. Although not wishing to be bound by theory, we believe that it is preferable to cut the plant material in slices or dices, preferably having a maximum width of 5 mm. The inventors indeed believe that it is important for the present invention in order to reach optimized thermodynamic exchanges.

The addition of fertilizers before the harvest of the plant material, acting as precursor of glucosamine allows to significantly increase the above-described reaction, from a few hundred mg of glucosamine per kg dry weight without precursor to at least 5 g glucosamine per kg dry matter of the corresponding plant material.

The process of the present invention generates glucosamine directly in free form. Without wishing to be bound by theory, it is believed that at least half of the glucosamine produced by said process is in free form, and even that almost all the glucosamine produced is in free form. Indeed, it is believed that at least 50%, at least 70%, and even at least 90% of the glucosamine is produced in free form according to the process of the invention. This is another advantage of the present invention compared to known techniques used to produce glucosamine, wherein an hydrolysis step is mandatory to release free glucosamine from complex molecules such as chitin, glycoproteins or proteoglycans, for example.

The plant or plant extract according to the invention may be used in the preparation of a food composition without further treatment or extraction. The said composition may be in the form of a nutritionally balanced food or pet food, a dietary supplement, a treat or a pharmaceutical composition.

EXAMPLES

The following examples are illustrative of some of the products and methods of making the same falling within the scope of the present invention. They are not to be considered in any way limitative of the invention. Changes and modifications can be made with respect to the invention. That is, the skilled person will recognize many variations in these examples to cover a wide range of formulas, ingredients, processing, and mixtures to rationally adjust the naturally occurring levels of the compounds of the invention for a variety of applications.

Example 1

Fresh Roots of Chicory (*Cichorium intybus*) Treated with Fertilizer During a Production Cycle of Chicons (Endives) in Hydroponic Cultures Roots of chicory are cultivated in hydroponic culture conditions during a current process for the production of endive for 21 days in dark at 20° C., 80% relative humidity. The nutritive solution contains 0.1M of ammonium sulfate. After 21 days, chicons and roots are harvested. The roots are cut in dices (0.5×0.5×0.5 cm) then dried in an oven at a temperature of 91° C. for 40 h.

Analysis:

Extraction of Glucosamine:

2 g of ground and specifically dried chicory root are extracted with 20 ml of water at room temperature for 1 minute. The solution is filtered on filter Schleicher & Schultz (n°597) or centrifuged. A purification step of the solution is performed using a cation exchange column (Oasis cartridge WATERS, MCX type, ref. 186 000 776). Basic compounds entrapped on the matrix are eluted with $MeOH/NH_4OH$ 2% (v/v). After filtration, an aliquot is used for direct injection on LC system (DIONEX).

Separation:

Analysis is carried out with a HPAE/PED system using an ion exchange PA1 column (4*250 mm) with DIONEX DX 500 apparatus.

Programme:

ELUTION (%)

| Time (min) | $H_2O$ | 0.1M NaOH | 0.25 NaOH | Comment |
|---|---|---|---|---|
| 0 | 85 | 15 | 0 | Balancing |
| 60 | 85 | 15 | 0 | |
| 60.1 | 0 | 0 | 100 | Washing |
| 70 | 0 | 0 | 100 | |
| 70.1 | 85 | 15 | 0 | Balancing |
| 90 | 85 | 15 | 0 | |

Flow: 1 ml/min. Volume of injection: 20 µl. Standard: Glucosamine from Sigma (ref: G4875).

In these conditions, glucosamine has a retention time of round 11 min and is easily detected for further quantification in chicory extracts properly processed. A concentration of 5000 mg/kg dry weight has been quantified by this method in the present example, instead of less than 900 mg/kg without precursor and less than 10 mg/kg without heating process or in commercial dried roots of chicory.

It is therefore possible to apply the present invention to plant materials producing endives, as a valorized by-product.

Confirmation of the Presence of Glucosamine:

In order to confirm the presence of glucosamine in chicory plant extracts, three different qualitative techniques have been evaluated.

Thin Layer Chromatography (TLC)

Pure glucosamine and plant extracts were analyzed on HPTLC (High Performance Thin Layer Chromatography) silica gel plates (Merck, ref. 1.05642) with Ethyl acetate/MeOH/water (50/50/10; V/V/V) as eluant. After elution, the plates are sprayed with an acetic acid solution of ninhydrine 1% and heated at 120° C. for 10 min. One spot appeared in a pink/blue color at the same rate factor (Rf) for the reference and extracts.

Chemical Degradation

In the presence of ninhydrine, an oxidative de-amination occurs with glucosamine, which leads to the release of arabinose easily detected through routine sugar LC analysis. Presence of arabinose with control and chicory extracts was unambiguously confirmed.

Derivatization of Glucosamine

Reverse phase chromatography using pre-column derivatization with phenylisothiocyanate and UV detection ($\lambda$=254 nm) was used with the pure compound and plant extracts as described by Zhongming et al.: "Determination of nutraceuticals, glucosamine hydrochloride in raw materials, dosage form and plasma using pre-column derivation with UV HPLC. In J. of Pharmaceut. and Biomed. Analysis, 1999 (20), 807-814."

The corresponding peak of derivatized glucosamine was detected in chicory extracts as well as with pure compound.

Mass Spectrum Analysis

Plant extracts were analyzed by Electrospray Mass Spectrometry in positive ionization mode to confirm the presence of glucosamine. The mass spectrometer was a time-of-flight instrument (LCT from Micromass with a Z-spray interface). Standard glucosamine give an ion at m/z 180.0887. This ion fragment is found in analyzed plant extracts.

Example 2

Fresh Roots of Chicory (*Cichorium intybus*) Treated with Fertilizer After a Production Cycle of Chicons (Endives) in Hydroponic Cultures After harvesting the endives grown under current conditions for usual commercial production, the residual roots are submitted to the same treatment. Roots are placed again in hydroponic culture conditions as in example 1 for a second culture cycle with the nutritive solution containing 1M of ammonium sulfate.

Roots are harvested at day 5 and then processed as described in example 1 (cutting, drying). It leads to a glucosamine concentration of 10 g/kg dry weight.

It is another example that it is possible to apply the present invention to plant materials producing endives, as a valorized by-product.

The invention claimed is:

1. A process for generating glucosamine from plants, the method comprising:
    adding a nitrogen-based fertilizer that acts as a glucosamine precursor during cultivation of a plant material, before harvest, wherein the plant material is a plant species belonging to a genus selected from the group consisting of *Cichorium, Daucus, Helianthus, Beta* and combinations thereof;
    harvesting the plant material; and
    heating the plant material in a form selected from the group consisting of non-dried plant materials, re-hydrated dried plant materials and plant extracts, to a temperature of between 70 and 110° C. for more than 10 hours, and less than one week to generate glucosamine from the plant material.

2. The process according to claim 1 wherein the fertilizer is a compound that allows the formation of a sugar-nitrogen compound condensation required to form glucosamine.

3. The process according to claim 1 wherein the plants are selected from the group consisting of chicory (*Cichorium intybus*), carrot (*Daucus carota*), Jerusalem artichoke (*Helianthus tuberosum*), and beet (*Beta vulgaris*).

4. The process according to claim 3 wherein chicory is produced in hydroponic conditions.

5. The process according to claim 4 wherein the fertilizer is added in a nutritive solution for a hydroponic cultivation of chicory roots before or after production of endives.

6. The process according to claim 5 wherein the resulting chicory roots of the endive production are used as a source of glucosamine.

7. A process for generating glucosamine, the method comprising:
    cultivating a plant material in a hydroponic culture system;
    adding a glucosamine precursor comprising a nitrogen-based fertilizer during cultivation of the plant material, before harvest, wherein the plant material is a plant species belonging to a genus selected from the group consisting of *Cichorium, Daucus, Helianthus, Beta* and combinations thereof;
    harvesting the plant material; and
    heating the plant material to a temperature of between 70 and 110° C. for more than 10 hours and less than one week to generate glucosamine from the plant material.

8. The process according to claim 1 wherein the fertilizer is ammonium salts.

9. The process according to claim 7 wherein the fertilizer is a compound that allows the formation of a sugar-nitrogen compound condensation required to form glucosamine.

10. The process according to claim 7 wherein the fertilizer is ammonium salts.

* * * * *